United States Patent
Richey et al.

(10) Patent No.: US 9,956,177 B2
(45) Date of Patent: May 1, 2018

(54) SUSTAINED RELEASE MICROSPHERES AND METHOD OF PRODUCING SAME

(71) Applicants: OAKWOOD LABORATORIES, Oakwood Village, OH (US); Tracy Richey, Kent, OH (US); Bagavathikanun Chithambara Thanoo, Brecksville, OH (US)

(72) Inventors: Tracy Richey, Kent, OH (US); Bagavathikanun Chithambara Thanoo, Brecksville, OH (US)

(73) Assignee: OAKWOOD LABORATORIES LLC, Oakwood Village, OH (US)

( * ) Notice: Subject to any disclaimer, the term of this patent is extended or adjusted under 35 U.S.C. 154(b) by 0 days. days.

(21) Appl. No.: 14/774,851

(22) PCT Filed: Mar. 14, 2014

(86) PCT No.: PCT/US2014/028657
§ 371 (c)(1),
(2) Date: Sep. 11, 2015

(87) PCT Pub. No.: WO2014/144309
PCT Pub. Date: Sep. 18, 2014

(65) Prior Publication Data
US 2016/0030351 A1  Feb. 4, 2016

Related U.S. Application Data

(60) Provisional application No. 61/790,554, filed on Mar. 15, 2013.

(51) Int. Cl.
*A61K 9/16*    (2006.01)
*A61K 31/573*  (2006.01)

(52) U.S. Cl.
CPC .......... *A61K 9/1694* (2013.01); *A61K 9/1647* (2013.01); *A61K 31/573* (2013.01)

(58) Field of Classification Search
None
See application file for complete search history.

(56) References Cited

U.S. PATENT DOCUMENTS

| | | | |
|---|---|---|---|
| 5,945,125 A | 8/1999 | Kim | |
| 6,046,187 A * | 4/2000 | Berde | A61K 31/57 514/180 |
| 6,270,802 B1 | 8/2001 | Thanoo et al. | |
| 6,392,036 B1 * | 5/2002 | Karlsson | A61K 9/0043 540/63 |
| 8,708,159 B2 * | 4/2014 | Thanoo | F04F 5/44 209/712 |
| 2005/0260272 A1 * | 11/2005 | Figueiredo | A61K 9/1641 424/489 |
| 2010/0086596 A1 * | 4/2010 | Thanoo | A61K 9/0019 424/486 |
| 2012/0205293 A1 * | 8/2012 | Thanoo | F04F 5/44 209/235 |

FOREIGN PATENT DOCUMENTS

| | | |
|---|---|---|
| GB | 2459910 | 11/2009 |
| WO | 2010/042870 | 4/2010 |
| WO | 2012/019009 | 2/2012 |
| WO | 2014144309 A1 | 9/2014 |

OTHER PUBLICATIONS

Chaw et al., "Water-soluble betamethasone-loaded poly(lactide-co-glycoside) hollow microparticles as a sustained release dosage form", J Microencapsulation 20: 349-359 (2003).*
Freitas S. L. P., "Novel strategies and technologies for the aseptic microencapsulation of pharmaceutical compounds", a dissertation presented 2005.*
Mohr et al., "Gamma irradiation for terminal sterilization of 17β-estradiol loaded poly-(D,L-lactide-co-glycolide) microparticles", J Controlled Release 61: 203-217 (1999).*
The ISR and Written Opinion of the International Searching Authority for PCT/US2014/028657, filed Mar. 14, 2014, pp. 1-13.
Chaw, C.S. et al., "Water-soluble betamethasoe-loaded poly(lactide-co-glycolide) hollow microparticles as a sustained drelease dosage form," Journal of Microencapsulation, 2003, vol. 20, No. 3, pp. 349-359.
Rafienia, M. et al., "In vitro evaluation of drug solubility and gamma irradiation on the release of betamethasone under simulated in vivo conditions," Journal of Bioactive and Compatible Polymers, 2007, vol. 22, No. 4, pp. 443-459.
Izumikawa, S. et al., "Preparation of poly(l-lactide) microspheres of different crystalline morphology and effect of crystalline morphology on drug release rate", Journal of Controlled Release, 1991, vol. 15, pp. 133-140.
Ishihara, T. et al., "Role of zinc in formulation of PLGA/PLA nanoparticles encapsulating betamethasone phosphate and its release profile", Journal of Controlled Release, 2005, vol. 105, pp. 68-76.
Higaki, M. et al., "Treatment of experimental arthritis with poly(d, L-lactic/glycolic acid) nanoparticles encapsulating betamethasone (Continued)

*Primary Examiner* — Robert A Wax
*Assistant Examiner* — Thor Nielsen
(74) *Attorney, Agent, or Firm* — Benesch, Friedlander, Coplan & Aronoff LLP (57) ABSTRACT

A method of making a sustained release microsphere formulation, wherein the release rate of a bioactive ingredient is manipulated by controlling the crystallinity of said bioactive ingredient, includes the steps of combining the active ingredient and an encapsulating polymer in at least one solvent, or mixtures thereof, to form a dispersed phase and processing the dispersed phase without filtering, filtering the combined dispersed phase with a hydrophobic or a hydrophilic filter, or filtering the active ingredient and encapsulating polymer individually with a hydrophobic or hydrophilic filter before combining them to form the dispersed phase. The dispersed phase is then combined with a continuous phase to form the microsphere formulation.

23 Claims, 5 Drawing Sheets

(56) References Cited

OTHER PUBLICATIONS sodium phosphate", Annals of the Rheumatic Diseases, 2005, vol. 64, pp. 1132-1136.

* cited by examiner

Figure 1: X-Ray Diffraction of Raw Materials and Physical Mixture

Figure 2: X-Ray Diffraction of Drug-Loaded Microspheres

SUSTAINED RELEASE MICROSPHERES AND METHOD OF PRODUCING SAME

RELATED APPLICATIONS

This application claims priority to U.S. Provisional Patent Application No. 61/790,554, filed on Mar. 15, 2013 and entitled Sustained Release Microsphere and Method of Producing the Same.

FIELD OF INVENTION

The present disclosure relates to a sustained release microsphere formulations and a method for producing the same. Specifically, the disclosure relates to a method of manufacturing a sustained released betamethasone microsphere formulation by controlling the crystallinity of the encapsulated drug.

BACKGROUND

Betamethasone is a potent corticosteroid steroid with anti-inflammatory and immunosuppressive properties. Unlike other drugs with these effects, betamethasone does not cause water retention. It is generally applied as a topical cream, ointment, foam, lotion or gel to treat itching. Betamethasone sodium phosphate has been prescribed as an intramuscular injection (IM) for itching from various ailments, including allergic reactions to poison ivy and similar plants, and to treat arthritis and other joint related diseases.

Currently, the delivery modes consist of systemic delivery or repeated intra-articular injections. These are fraught with serious complications. Direct intra-articular injection allows the use of compounds with low or no oral bioavailability. However, even then, the synovial membrane is a large and efficient resorptive surface, and highly soluble drugs are cleared rapidly, requiring frequent reinjections. It would therefore be beneficial to formulate a sustained release injection that has the potential to maintain a therapeutic drug level within the joint space over a period of several weeks to several months, decreasing the number of injections and injection-related side effects.

SUMMARY OF THE INVENTION

In one embodiment, a method of making a sustained release microsphere formulation, wherein the release rate of a bioactive ingredient is manipulated by controlling the crystallinity of said bioactive ingredient, includes the steps of (a) sterilizing an active ingredient with either heat or gamma sterilization to form a sterilized active ingredient; (b) dissolving an encapsulating polymer in a second solvent or mixtures thereof; (c) filtering the result of step (b); wherein said filtering is accomplished with a hydrophobic or hydrophilic filter; (d) combining the results from step (a) and step (c) to form a dispersed phase, wherein the result of step (a) is not filtered before it is combined with the result of step (c); and (e) combining the dispersed phase with a continuous phase to form the microsphere formulation.

In another embodiment, a method of making a sustained release microsphere formulation, wherein the release rate of a bioactive ingredient is manipulated by controlling the crystallinity of said bioactive ingredient, includes the steps of (a) sterilizing an active ingredient with either heat or gamma sterilization; (b) dissolving the active ingredient in a solvent or mixture thereof; (c) dissolving an encapsulating polymer in a solvent or mixture of solvents; (d) filtering the result of step (c); wherein said filtering is accomplished with a hydrophobic or hydrophilic filter; (e) combining the filtered solution from step (d) and the heat or gamma sterilized drug solution from step (b) to form a dispersed phase, wherein the result of step (e) is not sterile filtered further; and (f) combining the dispersed phase with a continuous phase to form the microsphere formulation.

Sterile filtration of a solution is achieved using 0.45 micron filter or smaller, preferably 0.2 micron filter. Even though the dispersed phase is not sterile filtered, it may be passed through a stainless steel sieve with pore size larger than 1 micron preferably larger than 5 micron to ensure the finished product does not have foreign particle contamination from drug source. Alternatively, the quality of the drug may be controlled at the site of manufacturing to be free of foreign particles.

In one embodiment, the encapsulating polymer may be selected from a polylactide or polylactide-co-glycolide, the active ingredient may be betamethasone, and the continuous phase may include polyvinyl alcohol.

A method of making a sustained release microsphere formulation, wherein the release rate of a bioactive ingredient is manipulated by controlling the crystallinity of said bioactive ingredient, includes the steps of combining the active ingredient and an encapsulating polymer in at least one solvent, or mixtures thereof, to form a dispersed phase and processing the dispersed phase without filtering, filtering the combined dispersed phase with a hydrophobic or a hydrophilic filter, or filtering the active ingredient and encapsulating polymer individually with a hydrophobic or hydrophilic filter before combining them to form the dispersed phase. The dispersed phase is then combined with a continuous phase to form the microsphere formulation.

BRIEF DESCRIPTION OF DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

A sustained release microsphere formulation including a corticosteroid, such as betamethasone, and a method of producing the same is provided. Specifically, the method of producing betamethasone microsphere formulations includes manipulating the drug release profile of the formulation by controlling the crystallinity of the encapsulated drug.

Many bioactive agents, such as small molecules, are crystalline, semi-crystalline, or amorphous in their raw form. Surprisingly, however, after an encapsulation process within a polymeric delivery system, the drug may or may not be in a crystalline state. Microspheres with encapsulated amorphous, semi-crystalline or crystalline drug compositions may be made by using appropriate filtration procedures of the dispersed phase. And, by altering the degree of crystallinity of the encapsulated drug using the appropriate filtration procedures, the release rate of the drug can be modified.

During microencapsulation of a drug, such as betamethasone, into a polymeric delivery system, the drug and polymer and polymer may be dissolved in a suitable solvent system, which is called the dispersed phase. To form a microsphere formulation, the dispersed phase is then combined with a continuous phase. The dispersed phase of the microsphere formulation may or may not be filtered prior to the encapsulation process. The dispersed phase may be sterile filtered to produce sterile end-product. However, alternate sterilization methods, such as gamma sterilization or heat sterilization may be performed on the end-product if appropriate.

Surprisingly, it has been discovered that for microspheres prepared with filtration of the dispersed phase, the degree of drug crystallinity depends on the type of filter material, or lack of filter material, used.

Examples

Six batches of microsphere were made using the following method. Betamethasone microspheres were prepared using a continuous water in oil (W/O) emulsification/solvent extraction procedure. Generally, a dispersed phase, including a biodegradable polymer of polylactide or polylactide-co-glycolide, a suitable solvent, and a pharmaceutically effective amount of betamethasone is prepared to form a clear homogeneous solution. The dispersed phase is then pumped in to a homogenizer, such as an in-line Silverson Homogenizer, commercially available from Silverson Machines, Waterside, UK, at a defined flow rate. Simultaneously, an aqueous continuous phase, including polyvinyl alcohol, is also pumped in to the homogenizer at a defined flow rate. The speed of the homogenizer is generally fixed to achieve a desired microsphere size distribution. This continuous microsphere process is described in U.S. Pat. No. 5,945,125, and is hereby incorporated by reference in its entirety.

The formed or forming microspheres exit the homogenizer and enter a solvent removal vessel (SRV). The resulting suspension is mixed in the SRV during the microsphere formation period. After the dispersed phase has been exhausted, the continuous and water flow rates are stopped, and the washing steps are initiated. Solvent removal is achieved using water washing and a hollow fiber filter (commercially available as HFF from GE Healthcare). This system previously is disclosed in U.S. Pat. No. 6,270,802, which is incorporated by reference herein in its entirety.

The washing steps begin by washing the microsphere suspension with room temperature water, followed by washing the suspension with hot water (about 38° C.) for approximately 60 minutes before cooling the suspension back down to room temperature.

The washed microspheres are then collected and freeze-dried overnight in a lyophilizer (Virtis) to remove all of the moisture. The resulting microspheres are a free-flowing off-white bulk powder.

For batch 1, a 19 wt % polymer solution was prepared by dissolving 250 g of a 100 PLA polymer (commercially available as R202H from Evonik, with an inherent viscosity of 0.183 dL/g) in 1060 g of dichloromethane (DCM) (commercially available from Spectrum Chemicals). Next, 47.6 g of betamethasone (commercially available from Sicor) was dissolved in 1706.8 g of benzyl alcohol (commercially available from Spectrum Chemicals). The two solutions were mixed together to obtain the dispersed phase. The dispersed phase was not sterile filtered before being combined with the continuous phase including polyvinyl alcohol in water.

For batch 2, a 19 wt % polymer solution was prepared by dissolving 250 g of a 100 PLA polymer (with an inherent viscosity of 0.183 dL/g) in 1060 g of DCM. Next, 52.5 g of betamethasone was dissolved in 1881 g of benzyl alcohol. The two solutions were mixed together to obtain the dispersed phase and was sterile filtered with a hydrophilic PVDF filter (commercially available from Pall) for the microsphere preparation.

For batch 3, a 31 wt % polymer solution was prepared by dissolving 285 g of a 100 PLA polymer (with an inherent viscosity of 0.183 dL/g) in 638 g of DCM. This solution was sterile filtered with a hydrophilic PVDF filter (commercially available from Pall). Next, 59.9 g of betamethasone was dissolved in 2144 g of benzyl alcohol and 570 g of DCM. The active ingredient solution was separately sterile filtered with a hydrophilic PVDF filter (commercially available from Pall). The filtered active ingredient solution and the filtered polymer solution solutions were mixed together to obtain the dispersed phase for the microsphere preparation. The dispersed phase was then combined with the continuous phase to form the microsphere formulation.

For batch 4, a 27 wt % polymer solution was prepared by dissolving 2.5 g of a 100 PLA polymer (with an inherent viscosity of 0.183 dL/g) in 6.6 g of DCM. This solution was sterile filtered with a hydrophobic PVDF filter (commercially available from Pall). Next, 0.525 g of betamethasone was dissolved in 18.8 g of benzyl alcohol and 7 g of DCM. This second solution was separately sterile filtered with a hydrophobic PVDF filter (commercially available from Pall). The two filtered solutions were mixed together to obtain the dispersed phase for the microsphere preparation. The dispersed phase was then combined with the continuous phase to form the microsphere formulation.

For batch 5, a 19 wt % polymer solution was prepared by dissolving 250 g of a 100 PLA polymer (with an inherent viscosity of 0.183 dL/g) in 1060 g of DCM. Next, 52.5 g of betamethasone was dissolved in 1881 g of benzyl alcohol. The two solutions were mixed together to obtain the dispersed phase and was sterile filtered with a hydrophobic PVDF filter (commercially available from Pall) for the microsphere preparation. The dispersed phase was then combined with the continuous phase to form the microsphere formulation.

For batch 6, a 7.8 wt % polymer solution was prepared by dissolving 250 g of a 100 PLA polymer (with an inherent viscosity of 0.183 dL/g) in 1060 g of DCM and 1881 g of benzyl alcohol. This polymer solution was sterile filtered using a hydrophobic PDVF filter (commercially available from Pall). 52.5 g of betamethasone was heat sterilized by heating the API at 160-170° C. for 120 minutes to form a heat sterilized drug powder. The filtered polymer solution then was added to the heat sterilized drug powder and mixed to form the dispersed phase. No subsequent filtration of this dispersed phase solution occurred and was used for the microsphere preparation. The dispersed phase was then combined with the continuous phase to form the microsphere formulation.

X-Ray Diffraction of Raw Materials and Physical Mixture

Figure 1:
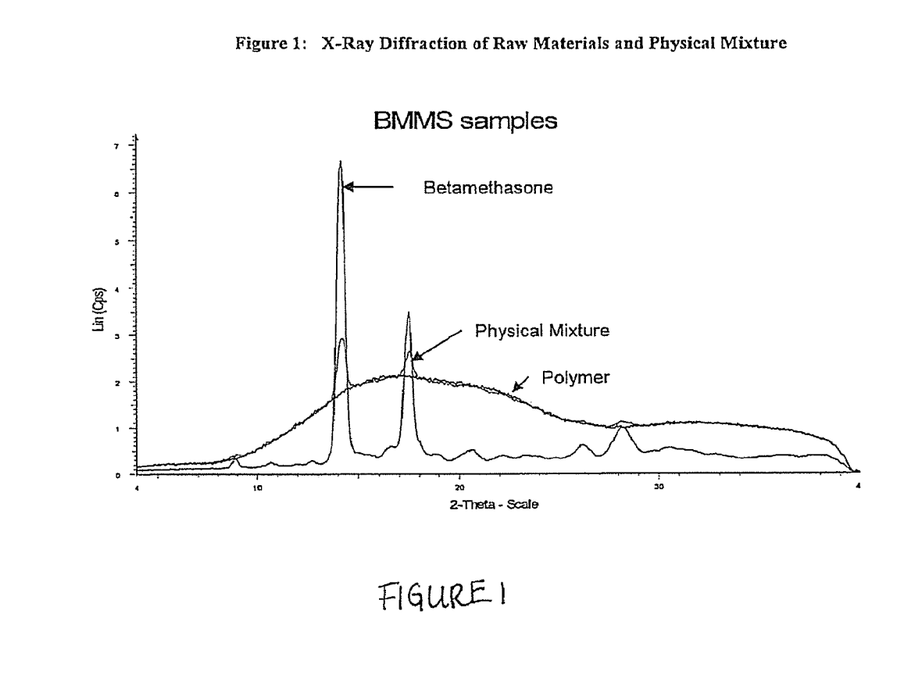
FIG. 1 is a graph comparing the diffraction pattern of the raw polymer, raw betamethasone, and the physical mixture of the two components.

The diffraction patterns of the raw polymer, raw betamethasone, and the physical mixture of the two (13 wt % betamethasone) were compared. As shown in FIG. 1, no sharp peaks are seen for the polymer, which is amorphous. The betamethasone powder, however is very crystalline, as evidenced by the numerous sharp peaks. The physical mixture of the polymer and betamethasone in the same weight ratio as in the microsphere shows the crystalline drug peaks superimposed on the polymer's amorphous pattern.

Figure 2:
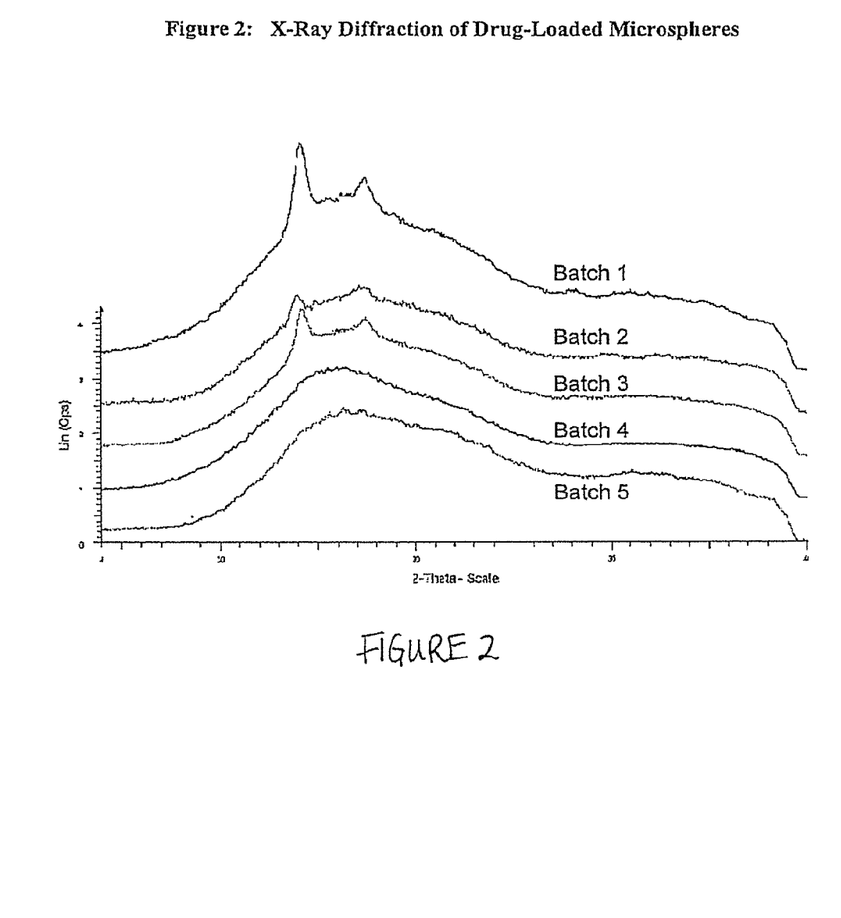
FIG. 2 is a graph comparing the diffraction pattern of five batches of betamethasone microsphere formulations with varying degrees of crystallinity.
Figure 3:
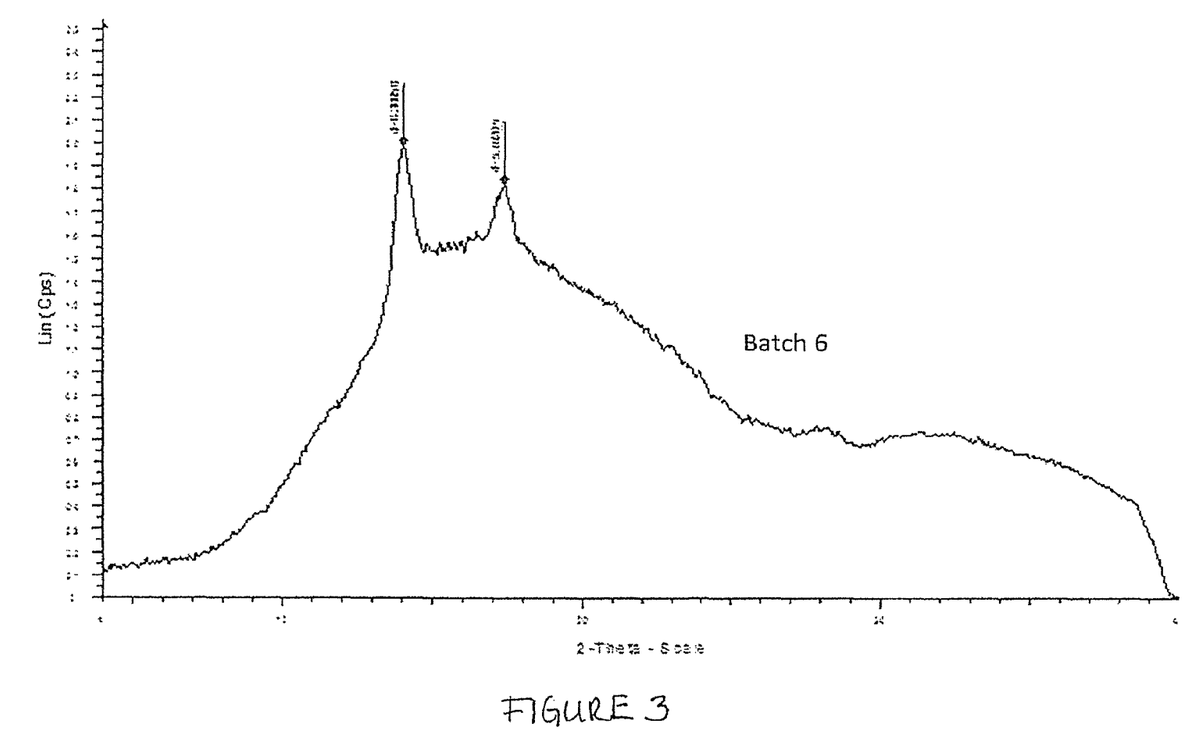
FIG. 3 is a graph illustrating the diffraction pattern of a batch of betamethasone microsphere formulations.

The diffraction patterns of the six batches were then obtained. As shown in FIGS. 2 and 3, batch 1, made without filtration of the dispersed phase and batch 6, made by heat sterilizing the betamethasone powder and combining the sterilized powder with a filtered polymer solution, had the highest degree of crystallinity, followed in order by batch 2, made by filtering the dispersed phase with a hydrophilic filter, batch 3, made by separately filtering the polymer and drug solutions with a hydrophilic filter, batch 4, made by separately filtering the polymer and drug solutions with a hydrophobic filter, and batch five, made by filtering the combined dispersed phase with a hydrophobic filter. Surprisingly, the method of filtration, or lack thereof, dramatically affected the crystallinity of the microsphere formulation.

Drug Release Under Physiological Conditions

Figure 4:
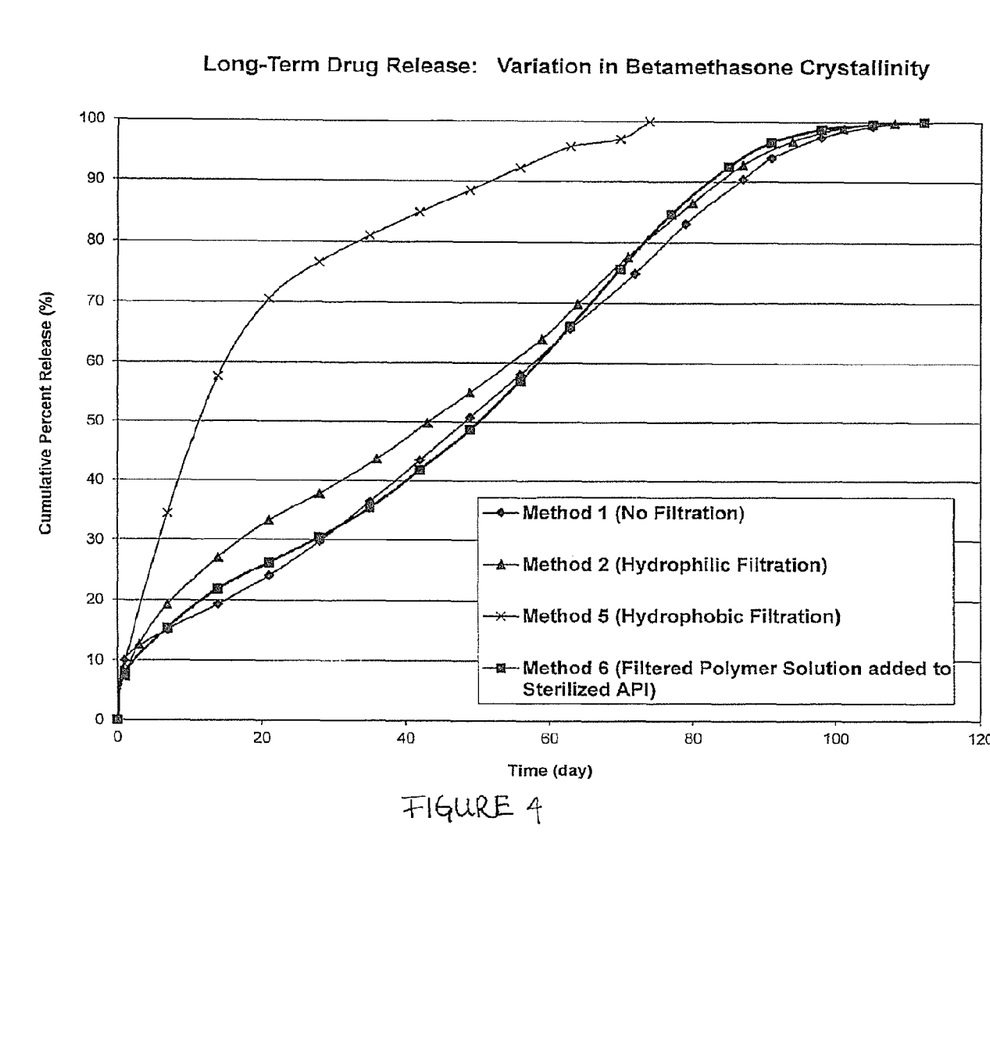
FIG. 4 is a graph comparing the long-term drug release of three batches betamethasone microsphere formulations.

The long term release was performed on betamethasone microspheres in a phosphate buffer under physiological conditions (pH around 7.4 and temperature around 37 C.). The modulation in release rate of the betamethasone formulations were compared for batches 1, a crystalline product, batch 2, a partially crystalline product, batch 5, an amorphous product, and batch 6, a substantially crystalline product and the cumulative percent release of betamethasone from the microspheres over time was plotted. As shown in FIG. 4, the microspheres produced using the hydrophobic filtration of the dispersed phase (batch 5) displayed a fast release profile, with most of the drug released within 40 days.

The microspheres produced using hydrophilic filtration of the dispersed phase (batch 2) displayed a slower release profile and the release profiles from microspheres of batch 1 and batch 6 were slower still, indicating that the increased crystallinity of the encapsulated drug changes the release rate of the drug in the system. Thus, through the manipulation of the encapsulated drug's crystallinity, the release of the betamethasone was expanded from about 40 days to over three months.

Drug Release Under Accelerated Conditions

Figure 5:
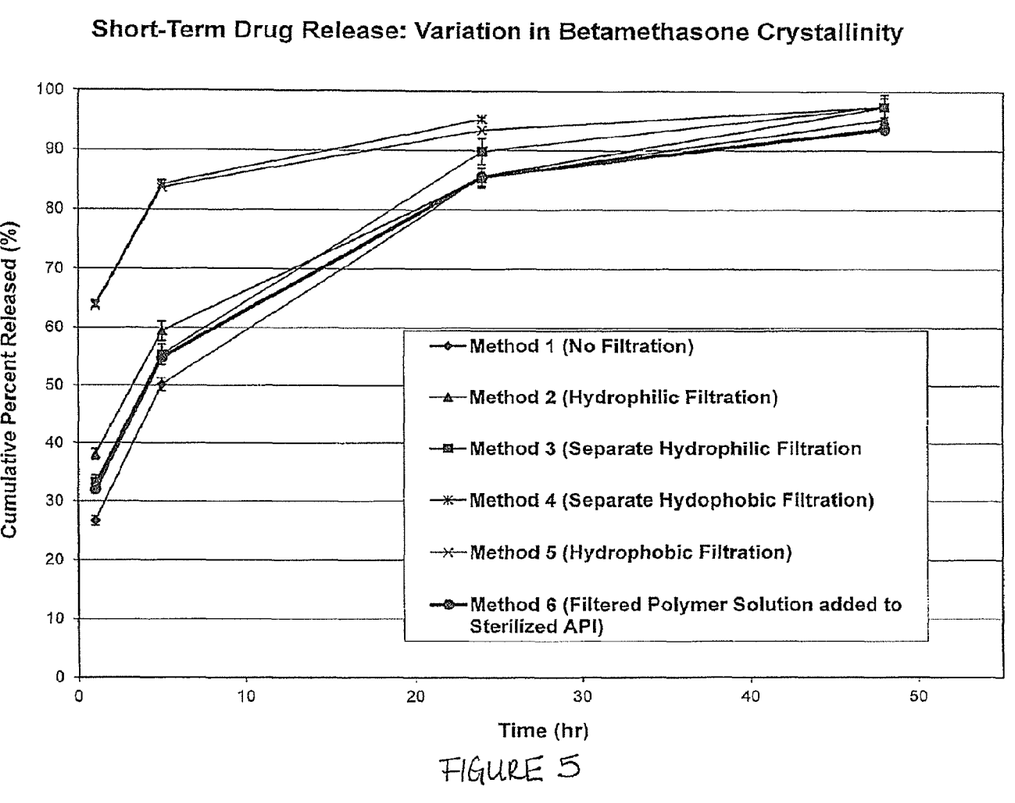
FIG. 5 is a graph comparing the short-term drug release of five batches of betamethasone microsphere formulations.

The short term release was performed on betamethasone microspheres under accelerated conditions, usually at a higher temperature than the long term release. As shown in FIG. 5, the accelerated short term release profiles of the five batches of microspheres were compared. Again, the release rate was much faster and duration of release shorter for the amorphous batch 5.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. A method of making a sustained release microsphere formulation, comprising the steps of:
   (a) sterilizing an active ingredient to form a sterilized active ingredient, wherein the active ingredient is betamethasone;
   (b) dissolving an encapsulating polymer in a solvent or mixture of solvents to form a polymer solution;
   (c) filtering the polymer solution with a hydrophobic or hydrophilic filter to form a filtered polymer solution;
   (d) combining the sterilized active ingredient, betamethasone and the filtered polymer solution to form a dispersed phase, wherein the sterilized active ingredient, betamethasone is not filtered before it is combined with the filtered polymer solution; and
   (e) combining the dispersed phase with a continuous phase to form the microsphere formulation,
   wherein the microsphere formulation prepared using the filtered polymer solution and sterilized active ingredient, betamethasone forms a highly crystalline active ingredient.

2. The method of claim 1, wherein the encapsulating polymer is selected from a polylactide or polylactide-co-glycolide.

3. The method of claim 1, wherein the sterilized active ingredient is dissolved in a solvent or solvent mixture before it is combined with the filtered polymer solution, but not sterile filtered.

4. The method of claim 1, wherein the continuous phase comprises polyvinyl alcohol.

5. The method of claim 1, wherein the solvent comprises dichloromethane, benzyl alcohol, or mixtures thereof.

6. The method of claim 1, wherein the active ingredient is sterilized using heat sterilization.

7. The method of claim 1, wherein the active ingredient is sterilized with gamma sterilization.

8. A method of making a sustained release microsphere formulation comprising the steps of:
   (a) dissolving an active ingredient in at least one solvent or a mixture of solvents to form an active agent solution, wherein the active ingredient is betamethasone;
   (b) filtering the active agent, betamethasone solution with a hydrophobic or hydrophilic filter;
   (c) dissolving an encapsulating polymer in a second solvent or second mixture of solvents to form a polymer solution;
   (d) filtering the polymer solution with a hydrophobic or hydrophilic filter;
   (e) combining the filtered active agent, betamethasone solution and the filtered polymer solution to form a dispersed phase; and
   (f) mixing the dispersed phase from step (e) with a continuous phase to form the microsphere formulation,
   wherein the microsphere formulation prepared by using a hydrophobic filter to filter the active agent, betamethasone solution in step (b) and the polymer solution in step (d) forms a less crystalline active agent compared to the microsphere formulation prepared by using a hydrophilic filter to filter the active agent, betamethasone solution in step (b) and the polymer solution in step (d).

9. The method of claim 8, wherein the encapsulating polymer is selected from a polylactide or polylactide-co-glycolide.

10. The method of claim 8, wherein the continuous phase comprises polyvinyl alcohol.

11. The method of claim 8, wherein the at least one solvent comprises dichloromethane, benzyl alcohol, or mixtures thereof.

12. The method of claim 8, wherein the second solvent comprises dichloromethane, benzyl alcohol, or mixtures thereof.

13. The method of claim 8, wherein the at least one solvent and the second solvent comprise dichloromethane, benzyl alcohol, or mixtures thereof.

14. A method of forming a sustained release microsphere formulation, comprising the steps of:
   (a) combining an active ingredient and an encapsulating polymer in at least one solvent, or mixture of solvents, to form a dispersed phase, wherein the active ingredient is betamethasone;
   (b) filtering the dispersed phase from step (a) to form a filtered dispersed phase, wherein the filtering step is accomplished with a hydrophobic or a hydrophilic filter; and
   (c) combining the filtered dispersed phase with a continuous phase to form the microsphere formulation,
   wherein the microsphere formulation prepared by filtering the dispersed phase with a hydrophobic filter forms amorphous active ingredient, betamethasone with a fast release profile, while the microsphere formulation prepared by filtering the dispersed phase with a hydrophilic filter forms a partially crystalline active ingredient, betamethasone with a slow release profile.

15. The method of claim 14, wherein the encapsulating polymer is selected from a polylactide or polylactide-co-glycolide.

16. The method of claim 14, wherein the continuous phase comprises polyvinyl alcohol.

17. The method of claim 14, wherein the at least one solvent comprises dichloromethane, benzyl alcohol, or mixtures thereof.

18. A sustained release formulation made according to the method of claim 1.

19. The sustained release formulation of claim 18, wherein the release of the betamethasone is from about forty days to about three months.

20. A sustained release formulation made according to the method of claim 8.

21. The sustained release formulation of claim 20, wherein the release of the betamethasone is from about forty days to about three months.

22. A sustained release formulation made according to the method of claim 14.

23. The sustained release formulation of claim 22, wherein the release of the betamethasone is from about forty days to about three months.

* * * * *